(12) United States Patent
Scavone et al.

(10) Patent No.: US 11,090,250 B2
(45) Date of Patent: Aug. 17, 2021

(54) COMPOSITIONS AND/OR ARTICLES COMPRISING CYCLODEXTRIN COMPLEXING MATERIAL

(71) Applicant: The Procter & Gamble Company, Cincinnati, OH (US)

(72) Inventors: Timothy Alan Scavone, Loveland, OH (US); Michael Jude Leblanc, Cincinnati, OH (US); Lowell Alan Sanker, Hamilton, OH (US); Adrian Gregory Switzer, Springboro, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 61 days.

(21) Appl. No.: 16/184,236

(22) Filed: Nov. 8, 2018

(65) Prior Publication Data

US 2020/0146965 A1 May 14, 2020
US 2021/0121388 A9 Apr. 29, 2021

Related U.S. Application Data

(63) Continuation of application No. 11/712,771, filed on Mar. 1, 2007, now Pat. No. 10,149,910.

(51) Int. Cl.
*A61Q 15/00* (2006.01)
*A61K 8/04* (2006.01)
*A61K 8/73* (2006.01)

(52) U.S. Cl.
CPC .............. *A61K 8/738* (2013.01); *A61K 8/046* (2013.01); *A61K 2800/57* (2013.01); *A61Q 15/00* (2013.01)

(58) Field of Classification Search
CPC .... A61K 8/046; A61K 8/738; A61K 2800/57; A61Q 15/00
See application file for complete search history.

(56) References Cited

U.S. PATENT DOCUMENTS

| | | | |
|---|---|---|---|
| 4,731,243 A | 3/1988 | Lindauer et al. |
| 4,803,195 A | 2/1989 | Holzner |
| 4,904,307 A | 2/1990 | Ammeraal et al. |
| 5,094,761 A | 3/1992 | Trinh et al. |
| 5,135,747 A | 8/1992 | Faryniarz et al. |
| 5,176,903 A | 1/1993 | Goldberg et al. |
| 5,378,468 A | 1/1995 | Suffis et al. |
| 5,380,707 A | 1/1995 | Barr et al. |
| 5,403,828 A | 4/1995 | Lewis et al. |
| 5,508,259 A | 4/1996 | Holzner et al. |
| 5,580,851 A | 12/1996 | Trinh et al. |
| 5,626,856 A | 5/1997 | Berndt |
| 5,660,845 A | 8/1997 | Trinh et al. |
| 5,711,941 A | 1/1998 | Behan et al. |
| 5,714,445 A | 2/1998 | Trinh et al. |
| 5,723,420 A | 3/1998 | Wei et al. |
| 5,733,272 A | 3/1998 | Brunner et al. |
| 5,780,020 A | 7/1998 | Peterson et al. |
| 5,861,144 A | 1/1999 | Peterson et al. |
| 5,874,067 A | 2/1999 | Lucas et al. |
| 5,879,666 A | 3/1999 | Lucas et al. |
| 5,882,638 A | 3/1999 | Dodd et al. |
| 5,897,854 A | 4/1999 | Lucas et al. |
| 5,897,855 A | 4/1999 | Trinh et al. |
| 5,932,198 A | 8/1999 | Goldman et al. |
| 5,976,514 A | 11/1999 | Guskey et al. |
| 6,036,964 A | 3/2000 | Guenin et al. |
| 6,110,449 A * | 8/2000 | Bacon .................... A61K 8/738 422/5 |
| 6,123,932 A * | 9/2000 | Guskey .................. A61K 8/042 422/5 |
| 6,165,452 A | 12/2000 | Boden et al. |
| 6,180,121 B1 | 1/2001 | Guenin et al. |
| 6,287,603 B1 | 9/2001 | Prasad et al. |
| 6,306,818 B1 | 10/2001 | Anderson et al. |
| 6,495,097 B1 | 12/2002 | Streit et al. |
| 6,509,010 B2 | 1/2003 | Beck et al. |

(Continued)

FOREIGN PATENT DOCUMENTS

| CN | 1054605 A | 9/1991 |
|---|---|---|
| EP | 0535942 A3 | 4/1993 |

(Continued)

OTHER PUBLICATIONS

International Search Report and Written Opinion of the International Searching Authority, PCT/IB2008/050733, dated Apr. 14, 2009, 14 pages.

(Continued)

*Primary Examiner* — Zohreh A Fay
(74) *Attorney, Agent, or Firm* — Kathleen Y. Carter

(57) ABSTRACT

Personal care products are provided. An exemplary personal care product includes a composition that is applied to the body or clothing, or an article applied against the body; a plurality of particles associated with the composition or a component of the article, the plurality of particles, at least some of the plurality of particles comprising a cyclodextrin complexing material and a first fragrance material, wherein the percent of the first fragrance material that is complexed with the cyclodextrin is greater than about 90%, so that the perceptibility of the first fragrance is minimized prior to its release; and a second fragrance material that is not complexed with the cyclodextrin and that is different from the first fragrance material, wherein the composition or article does not contain an antiperspirant active.

11 Claims, No Drawings

(56) References Cited

U.S. PATENT DOCUMENTS

| | | |
|---|---|---|
| 6,793,915 B1 | 9/2004 | Guenin et al. |
| 6,805,855 B2 | 10/2004 | Mattai et al. |
| 6,824,763 B2 | 11/2004 | Brooks |
| 6,835,373 B2 | 12/2004 | Kolodzik et al. |
| 6,893,647 B1 | 5/2005 | Malton et al. |
| 7,041,337 B2 | 5/2006 | Heltovics et al. |
| 7,208,462 B2 | 4/2007 | Heltovics et al. |
| 7,208,463 B2 | 4/2007 | Heltovics et al. |
| 7,208,464 B2 | 4/2007 | Heltovics et al. |
| 7,208,465 B2 | 4/2007 | Heltovics et al. |
| 7,407,650 B2 | 8/2008 | Heltovics et al. |
| 7,413,731 B2 | 8/2008 | Heltovics et al. |
| 8,632,755 B2 | 1/2014 | Scavone et al. |
| 9,649,386 B2 | 5/2017 | Scavone et al. |
| 9,649,387 B2 | 5/2017 | Scavone et al. |
| 2002/0025946 A1 | 2/2002 | Buchanan et al. |
| 2003/0049290 A1 | 3/2003 | Jha et al. |
| 2003/0060379 A1 | 3/2003 | Souter et al. |
| 2003/0069165 A1 | 4/2003 | Malton et al. |
| 2003/0087776 A1 | 5/2003 | Heltovics et al. |
| 2003/0119713 A1 | 6/2003 | Heltovics et al. |
| 2003/0194416 A1 | 10/2003 | Shefer et al. |
| 2003/0198680 A1 | 10/2003 | Shefer et al. |
| 2003/0211125 A1 | 11/2003 | Heltovics et al. |
| 2003/0232025 A1 | 12/2003 | Colwell et al. |
| 2004/0001891 A1 | 1/2004 | Smith et al. |
| 2004/0091435 A1 | 5/2004 | Shefer et al. |
| 2004/0109833 A1 | 6/2004 | Tang et al. |
| 2004/0175404 A1 | 9/2004 | Shefer et al. |
| 2004/0202632 A1 | 10/2004 | Gott et al. |
| 2005/0003975 A1 | 1/2005 | Browne et al. |
| 2006/0243322 A1 | 11/2006 | Heltovics et al. |
| 2006/0263313 A1 | 11/2006 | Scavone et al. |
| 2006/0292098 A1 | 12/2006 | Scavone et al. |
| 2008/0213191 A1 | 9/2008 | Scavone et al. |
| 2008/0213203 A1 | 9/2008 | Scavone et al. |
| 2008/0213204 A1 | 9/2008 | Scavone et al. |
| 2009/0214446 A1 | 8/2009 | Strassburger |

FOREIGN PATENT DOCUMENTS

| | | |
|---|---|---|
| EP | 0392608 B1 | 6/1995 |
| EP | 1024785 B1 | 1/2003 |
| EP | 0966258 B1 | 5/2003 |
| EP | 0965326 B1 | 7/2007 |
| JP | S63-035517 A | 2/1988 |
| JP | H10-120541 A | 5/1998 |
| JP | H10-263062 A | 10/1998 |
| JP | H11-209784 A | 8/1999 |
| JP | 2002-37722 A | 2/2002 |
| WO | WO98/18439 | 5/1998 |
| WO | WO 98/56340 | 12/1998 |
| WO | WO2004/078154 | 9/2004 |
| WO | WO 2006/137958 A1 | 12/2006 |

OTHER PUBLICATIONS

All Office Actions, U.S. Appl. No. 11/712,739.

Del Valle, Cyclodextrins and their uses: a review, Process Biochemistry, vol. 39 (2004), pp. 1033-1046.

Hedges, Industrial Applications of Cyclodextrins, Chemical Reviews, 1998, vol. 98, pp. 2035-2044.

* cited by examiner

COMPOSITIONS AND/OR ARTICLES COMPRISING CYCLODEXTRIN COMPLEXING MATERIAL

CROSS REFERENCE TO RELATED APPLICATION

This application is a continuation of prior U.S. application Ser. No. 11/712,771, filed on Mar. 1, 2007.

FIELD OF THE INVENTION

The present invention is directed to personal care products containing cyclodextrin complexing material and a fragrance material complexed with the same.

SUMMARY OF THE INVENTION

The present invention is directed to personal care products, including compositions that are applied to the body or clothing, and articles that are worn or applied against the body. The compositions can include, but are not limited to, body sprays, deodorant products (applied to the body and/or clothing (e.g., via a dryer sheet)), detersive products, fabric softeners, skin care products, hair care products, shaving compositions, and personal cleansing products (e.g., cleansing bars and body washes). The articles may include, but are not limited to, wipes, patches, and absorbent articles. Exemplary absorbent articles include diapers, feminine hygiene products, incontinence products, and wound dressings. The compositions and articles comprise a plurality of particles that include a cyclodextrin complexing material and a fragrance material complexed with the same. The particles may be manufactured to provide a high level of complexing efficiency. That is, a majority of the fragrance is bound to the interior of the cyclodextrin molecules, so that the perceptibility of the fragrance is minimized prior to its release. The particles may also have relatively low levels of moisture to help minimize the potential for microbial growth in the compositions or articles. Particles having relatively low levels of the moisture may also have a reduced tendency to agglomerate. Agglomerated particles can lead to a grainy or gritty feel associated with the composition or articles. Since the personal care products of the present invention include compositions that are applied to the body and articles that are worn/applied against the body, a grainy or gritty feel is likely undesirable for a significant number of users.

In accordance with some of the preferred embodiments, there has now been provided a personal care product comprising a composition that is applied to the body or clothing, or an article applied against the body; and a plurality of particles associated with the composition or a component of the article, the plurality of particles, at least some of the plurality of particles comprising a cyclodextrin complexing material and a fragrance material, wherein the percent of the fragrance material that is complexed with the cyclodextrin is greater than about 90%, so that the perceptibility of the fragrance is minimized prior to its release, and wherein the composition does not contain an antiperspirant active.

In accordance with another preferred embodiment, there has now been provided a personal care product comprising a composition that is applied to the body or clothing, or an article applied against the body; and a plurality of particles associated with the composition or a component of the article, at least some of the plurality of particles comprising a cyclodextrin complexing material and a fragrance material, wherein the plurality of particles are formed using a process comprising a step of spray drying, and wherein the composition does not contain an antiperspirant active.

In accordance with yet another preferred embodiment, there has now been provided a personal care product comprising a composition that is applied to the body or clothing, or an article applied against the body; and a plurality of particles associated with the composition or a component of the article, the plurality of particles comprising a cyclodextrin complexing material and a fragrance material, at least some of which being complexed with the cyclodextrin, wherein the plurality of particles has a moisture level, before their association with the composition or article component, of less than about 20% by weight of the particles, wherein the composition does not contain an antiperspirant active.

The above-described personal care products may further comprise a second fragrance material that is not complexed with the cyclodextrin and that is different from the complexed fragrance. Alternatively, these personal care products may be substantially free of other fragrances and be marketed with terms including "unscented," "scent-free," "hypoallergenic," and "sensitive."

The preferred embodiments described above explicitly exclude an antiperspirant active. However, other preferred embodiments can include such an active. In accordance with one of these preferred embodiments, there has now been provided a personal care product, comprising an aqueous carrier material; and a plurality of particles disposed in the aqueous carrier material, the plurality of particles comprising a cyclodextrin complexing material and a fragrance material, wherein the percent of the fragrance material that is complexed with the cyclodextrin is greater than about 90%, so that the perceptibility of the fragrance is minimized prior to its release, and wherein the plurality of particles are coated with a hydrophobic coating material to minimize premature release due to the presence of the aqueous carrier material.

In accordance with another of these preferred embodiments, there has now been provided a personal care product, comprising an aqueous carrier material; and a plurality of particles disposed in the aqueous carrier material, the plurality of particles comprising a cyclodextrin complexing material and a fragrance material, wherein the plurality of particles are formed using a process comprising a step of spray drying, and wherein the plurality of particles are coated with a hydrophobic coating material to minimize premature release due to the presence of the aqueous carrier material.

In accordance with another preferred embodiment, there has now been provided a personal care product, comprising a liquid carrier; an antiperspirant active dispersed within the liquid carrier; and a plurality of particles dispersed within the liquid carrier, the plurality of particles comprising a cyclodextrin complexing material and a fragrance material, wherein the percent of the fragrance material that is complexed with the cyclodextrin is greater than about 90%, so that the perceptibility of the fragrance is minimized prior to its release, wherein the personal care product is in the form of a spray, a roll-on, or an aerosol.

In accordance with yet another preferred embodiment, there has now been provided a personal care product, comprising a liquid carrier; an antiperspirant active dispersed within the liquid carrier; and a plurality of particles dispersed within the liquid carrier, the plurality of particles comprising a cyclodextrin complexing material and a fragrance material, wherein the plurality of particles are formed using a process comprising a step of spray drying, wherein the personal care product is in the form of a spray, a roll-on, or an aerosol.

DETAILED DESCRIPTION OF THE INVENTION

The present invention may be understood more readily by reference to the following detailed description of illustrative and preferred embodiments. It is to be understood that the scope of the claims is not limited to the specific features, methods, conditions, or parameters described herein, and that the terminology used herein is for the purpose of describing particular embodiments by way of example only and it not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The personal care products of the present invention comprise cyclodextrin complexing material and a fragrance material complexed with the same. The personal care products include compositions that are applied to the body or clothing, and articles that are worn or applied against the body. Exemplary compositions contemplated by the present invention include body sprays, deodorant products, detersive products, skin care products, hair care products, shaving compositions, and personal cleansing products (e.g., personal cleansing bars and body washes). When the personal care products are in the form of a composition, the cyclodextrin-fragrance complexes are simply added as one of the ingredients.

When the personal care products are in the form of an article, the cyclodextrin-fragrance complexes may be loosely employed between two or more layers/components of the article and/or adhered to a layer or component of the article with a suitable adhesive, such as, for example, a styrene-based block copolymer. The personal care products can include wipes, patches, and the like. The personal care products of the present invention can also include absorbent articles, for example, diapers, feminine hygiene products, incontinence products, and wound dressings. Absorbent articles typically include a liquid permeable top sheet or cover layer, a liquid impermeable back sheet or layer, and an absorbent core disposed therebetween. The articles may include additional components, such as, for example, a transfer layer underlying the top sheet that both facilitates quick fluid transfer from the top sheet to the absorbent core and deters fluid from leaving the absorbent core after the acquisition (i.e., deters "rewet" or "squeeze out"). Exemplary top sheets and transfer layers can include nonwovens, woven sheets, and apertured films. Exemplary absorbent cores can include wood pulp, hydrogels, absorbent polymers, and the like. And exemplary back sheets can include a polyolefin film. As noted above, the complexes may reside loosely between one or more of these absorbent article components and/or may be adhered to the same via an appropriate adhesive.

In some of the preferred embodiments of the present invention, the personal care products include a first fragrance material complexed with cyclodextrin, and a second uncomplexed fragrance material that is different from the first fragrance material. This design yields an initial scent expression with a different follow-up or secondary scent expression upon release of the second fragrance material.

In other preferred embodiments of the present invention, the personal care products include a fragrance material complexed with cyclodextrin, and is substantially free of any other fragrance material. In these embodiments, an initial scent expression is limited, preferably to a point where it is effectively "hidden" to consumers. Accordingly, these personal care products may be marketed using terms such as, for example, "unscented," "scent-free," "hypoallergenic," and/or "sensitive." A triggering mechanism (e.g., flowing of bodily fluids) or exposure to fluids will release the fragrance to provide an expression that is then perceived by the consumer.

Exemplary cyclodextrin complexing material, fragrance material, and methods of manufacturing complexes are discussed below. One exemplary embodiment provided herein Cyclodextrin Complexing Material Personal care products of the present invention include a cyclodextrin complexing material for substantially "hiding" a fragrance material until a triggering mechanism has occurred, such as, for example, perspiration, urination, menstruation, to "release" the fragrance material. As used herein, the term "cyclodextrin" includes any of the known cyclodextrins such as unsubstituted cyclodextrins containing from about six to about twelve glucose units, especially alpha-cyclodextrin, beta-cyclodextrin, gamma-cyclodextrin and/or their derivatives and/or mixtures thereof. For example, the present invention may use cyclodextrins selected from the group consisting of beta-cyclodextrin, hydroxypropyl alpha-cyclodextrin, hydroxypropyl beta-cyclodextrin, methylated-alpha-cyclodextrin, methylated-beta-cyclodextrin, and mixtures thereof. Cyclodextrins may be included within the personal care products from at least about 0.1%, from at least about 1%, from at least about 2%, or from at least about 3% to about 25%, to about 20%, to about 15% or to about 10%, by weight of the composition or article component.

Cyclodextrin particles and cyclodextrin complexes comprising a fragrance material can be formed by various methods. For example, a solvent (e.g., water), unloaded cyclodextrin particles, and a fragrance material can be placed into a container and then mixed for a period of time to permit loading of fragrance molecules into "cavities" of cyclodextrin molecules. The mixture may or may not be processed further; e.g., processed through a colloid mill and/or homogenizer. The solvent is then substantially removed from the resulting mixture or slurry to yield cyclodextrin complex particles. Different manufacturing techniques may however impart different particle/complex characterizations, which may or may not be desirable in the personal care product. In accordance with some of the preferred embodiments of the present invention, the particles and/or complexes have a low level of moisture prior to their inclusion into the personal care product. For a given volume of cyclodextrin particles (at least some of which being complexed with a fragrance material), it is preferred to have a moisture level of less than about 20% by weight of the particles, more preferred to have a moisture level of less than about 10% by weight of the particles, and even more preferred to have a moisture level of less than about 6% by weight of the particles, prior to the inclusion of the volume of particles into the composition. Other moisture levels may be suitable for personal care products of the present invention; accordingly, these preferred levels should not be read into claims that do not specify a cyclodextrin particle/complex moisture level.

Spray drying a slurry or mixture of cyclodextrin-fragrance complexes is one manufacturing technique capable of producing the cyclodextrin particles and cyclodextrin complexes having the above-noted, preferred moisture levels. Table I below provides a comparison of spray dried cyclodextrin complexes versus complexes formed via an extruder process (kneading).

TABLE I

Cyclodextrin Complex Moisture Level

| Sample | % Moisture |
|---|---|
| Spray Dry Process Sample A | 4.4 |
| Spray Dry Process Sample B | 3.7-4.5 |
| Spray Dry Process Sample C | 5.3 |
| Extruder Process Sample A | 27.87 |
| Extruder Process Sample B | 27.97 |
| Extruder Process Sample C | 24.00 |

Water content, USP (United States Pharmacopeia, current as of Aug. 1, 2006) <921> Method I is the analytical method for determining cyclodextrin complex moisture level, as shown in Table I.

As one can see from Table 1, the moisture level directly manifested by these two methods is dramatically different. It should be understood that this comparison is not intended to disclaim kneading/extruder processes from appended claims that do not specify a particular complex formation process. Rather, a kneading and extrusion method, or other method forming particles/complexes with higher than desired moisture levels, would require additional processing after their initial formation. For example, extruded complexes may require processing through an oven or dryer, or exposure to a controlled environment for a period of time.

Although not wishing to be bound by theory, it is believed that cyclodextrin particles/complexes having a relatively high moisture level have an increased tendency to agglomerate. The agglomerated particles may reach a size so as to become perceptible by a consumer; that is, a consumer may characterize the composition as being "gritty." And a "gritty" antiperspirant composition may not be desirable to some consumers, particular in solid product forms where the product is rubbed against the body as the means of applying the antiperspirant. Microbial growth is another potential disadvantage associated with employing cyclodextrin particles/complexes with relatively high moisture levels into a final composition depending on the remaining ingredients of the composition and/or storage parameters.

The efficiency or level of complexing with a fragrance material is another parameter of cyclodextrin complexes that can vary greatly depending on the manufacturing techniques employed. Put another way, the percent of fragrance material that is associated with the interior of a cyclodextrin molecule compared to the percent of fragrance material that is associated with the exterior of the cyclodextrin complex. The fragrance material that is on the exterior region of the complex is essentially free to be expressed without the requirement of a triggering mechanism, such as perspiration. The probability that a consumer perceives the fragrance material prior to a triggering mechanism increases as the level of free fragrance increases. And perception of a fragrance material prior to a triggering mechanism may not be desired depending on the overall composition design and targeted benefit associated with employment of the cyclodextrin complexes. In accordance with at least some of the preferred embodiments, the percent of fragrance material that is complexed with cyclodextrin is greater than about 75%, in some instances greater than about 90%, and in other instances greater than about 95%. It should be understood that these levels of fragrance complexation are directly associated with the complex formation process itself; the percentages do not represent a formulation design of adding a first percentage of fragrance material via a cyclodextrin complex and adding a second percentage of neat fragrance material.

Spray drying a slurry or mixture of cyclodextrin-fragrance complexes is one manufacturing technique capable of producing cyclodextrin complexes having the above-noted levels of fragrance complexation. Table II below provides a comparison of spray dried cyclodextrin complexes versus complexes formed via an extruder process (kneading).

TABLE II

Percent of Fragrance Loading in Cyclodextrin Complexes

| Sample | Complexation Efficiency |
|---|---|
| Spray Dry Process Sample A | 96.6 |
| Spray Dry Process Sample B | 96.8 |
| Spray Dry Process Sample C | 96.2 |
| Extruder Process Sample A | 60.77 |
| Extruder Process Sample B | 65.47 |
| Extruder Process Sample C | 67.07 |

One can see from Table II that spray drying is capable of producing cyclodextrin complexes with very little free fragrance as compared to a kneading/extruder process. The skilled artisan should appreciate that the comparison provided in Table II is not intended to disclaim kneading/extruder processes from appended claims that do not specify a particular complex formation process. Rather, additional processing steps may, for example, need to be employed to eliminate free fragrance associated with extruded complexes prior to their inclusion into a composition.

The analytical method for determining the percent of fragrance complexed, as shown in Table II, determines the free fragrance level in the complex by dissolving a sample in tetrahydrofuran (THF) adding an internal standard, and analyzing by capillary gas chromatography (GC). The complexed fragrance level is measured by extracting the same sample in acetone containing an internal standard, and analyzing by GC.

Complexation Efficiency=% Complexed/[% Complexed+% Free]

Original Sample Preparation

Internal Standard Stock Solution (ISSS)

Weigh 0.625 g±0.05 g of Diphenyloxide into a tared 100 mL volumetric flask and make to volume with acetone (Baker HPLC grade 9254-03). This is a suggested internal standard, other materials may be substituted as necessary to avoid chromatographic overlap depending on the specific fragrance to be analyzed.

Standards

Select a sufficient number (typically 10-20) of fragrance components to account for 80% or greater of the total area of the fragrance chromatogram. A synthetic blend of these components will be the primary standard used to quantitate fragrance levels. A sample of the fragrance is used as the secondary standard which enables correction for the fact that less than 100% of the components are calibrated.

Primary Standard Calibration Solutions

Primary stock: Weigh 0.1 g (to 0.001 g) of the individual fragrance components to be quantitated into a tared 100 mL volumetric flask and record the weights. Make to volume with acetone. Pipette 3.0 mL of the primary stock into a 50 mL volumetric flask and add 0.50 mL of ISSS for complexed calibration standard and dilute to volume with acetone. Pipette 3.0 mL of the primary stock into a 50 mL volumetric flask and add 0.50 mL of ISSS for neat calibration standard and dilute to volume with THF (Baker 9450-03).

Secondary Fragrance Standard Calibration Solutions

Secondary stock: Weigh 0.5 g (±0.1 g with precision to 0.0001 g) of the fragrance into a tared 100 mL volumetric flask and record weight. Make to volume with extraction solution for total fragrance (acetone); mix well. Pipette 3.0 mL of the secondary stock into a 50 mL volumetric flask and add 0.50 mL of ISSS for complexed fragrance standard and dilute to volume with acetone. Pipette 3.0 mL of the secondary stock into a 50 mL volumetric flask and add 0.50 mL of ISSS for neat fragrance standard and dilute to volume with THF.

Preparation of Samples

The ASE Solvent Extractor used in these analyses was a Dionex 200. Insert fiber filter (Dionex #49458) into an 11 mL cell body (Dionex part number 47004) with end cap on one end. Push filter to meet end cap. Tare on balance. Carefully add 1.000 gram (+/−0.250 grams) of sample to cell and record actual weight. Using a funnel, add sand (30-40 mesh, EM Science EM-SX0075-1 or alternate inert material) to fill the cell, place another fiber filter on top and close cell with second end cap. Use care in applying this filter so it is not above the end of the cell but rather push down slightly so the filter is inside the walls of the cell. This is to avoid filter particles from accumulating within the threads of the end caps which can cause leaking during extraction. Record cell serial number to correspond with sample identification. Load the cells and their corresponding collection vials (60 ml Dionex 48784) onto the ASE. [Note: For each sample two collection vials will be needed, one for the THF extraction (neat fragrance) and one for the acetone extraction (complex fragrance). To extract multiple samples it is recommended that all the THF extractions be done prior to the acetone extractions due to the temperature difference between the two methods.]

ASE Methods

| THF - Neat Fragrance | Extraction | Acetone - Complexed |
|---|---|---|
| 0 min | Preheat | 0 min |
| 5 min | Heat | 6 min |
| 4 min | Static | 15 min |
| 100% | Flush | 100% |
| 60 sec | Purge | 60 sec |
| 1 | Cycles | 3 |
| 500 psi | Pressure | 2000 psi |
| 40° C. | Temperature | 110° C. |
| 100% THF | Solvent | 100% Acetone |

Preparation of ASE

Assure sufficient nitrogen flow by verifying pressures for solvent bottles are at 10 psi, system air is at 50 psi and compression oven is at 130 psi. Verify there is an adequate amount of nitrogen to complete the run. Typically 1000 psi of nitrogen is used to extract 15 samples. Enter ASE methods, above, and save each method under a separate number. For example: The THF method can be saved as number 1 and the acetone method can be saved as number 2. Verify there is an adequate volume of both THF and acetone present to complete the run. Approximately 30 mL of each solvent is used per sample (note: usage can vary from system to system). With rinse collection vials present and an adequate volume of THF present, rinse the system with THF a few times to prime lines and remove any air. With cells and their corresponding labeled collection vials in place, the ASE methods are ready to begin.

Post ASE Sample Preparation for Complexed Fragrance (in Acetone)

Remove ASE collection vials containing complexed fragrance extract. Screw off the cap on the collection vial. Add 0.50 mL of ISSS directly to the collection vial, with a volumetric pipet. Add approximately 30 mL of acetone. Replace the cap onto the collection vial tightly. Shake well for approximately 30 seconds.

Post ASE Sample Preparation for Neat Fragrance (in THF)

Remove ASE collection vials containing neat fragrance extract. Screw off the cap on the collection vial. Add 0.50 mL of ISSS directly to the collection vial, with a volumetric pipet. Add approximately 30 mL of tetrahydrofuran. Replace the cap onto the collection vial tightly. Shake well for approximately 30 seconds.

Apparatus Criteria (Suggested Type or Source)

Gas Chromatograph HP5890 or equivalent equipped with capillary inlet system.

and flame ionization detector with peak integration capabilities

Column DB-5 column, 30 m×0.32 mm I.D. with 1.0 micron coating, J&W Scientific cat. no. 123-5033

Gas Chromatographic Conditions

Carrier Gas Helium UHP grade or regular grade helium purified through a dry tube and an oxygen scrubber. Flow-pressure regulated at 15 psi with 30 mL/min. split flow.

Oven Temperature. 50° C.-250° C. @ 6° C./min; 250° C.-315° C. @ 70° C./min.; Hold at 315° C. for 5 minutes Injector Temperature 250° C.

Detector Temperature 325° C.

Hydrogen and Air Flows Optimized for gas chromatograph used

Integration Threshold 2, peak width 0.04 Injection 1 microliter: splitless mode

Calculations

% Analyte=[(AvRf)(A)(B)×100]/[C×D] Where:

AvRf=Average response factor for standard sample
A=Weight of internal standard added to sample solution
B=Area of analyte peak in sample chromatogram
C=Area of internal std. peak in sample chromatogram
D=Sample weight in gram
100=Factor for percent conversion Corrected % Complexed or % Free in samples=[sum of the % of all individual fragrance components in sample×100]/[sum of the % of all individual fragrance components in the sec. std.]

The cyclodextrin complexes may be coated to minimize premature release/activation. Generally, any material that is capable of resisting water penetration is suitable. The coating material may include, for example, hydrocarbons, waxes, petrolatum, silicones, silicone derivatives, partially or fully esterfied sucrose esters, and polyglycerol esters. Using petrolatum as an example, a coating process may include combining cyclodextrin complexes with petrolatum at a ratio of about 1:1, for example, and then mixing until the complexes are satisfactorily coated.

Another technique for delaying release or activation of a complexed fragrance, as contemplated herein, is to combine the fragrance material with an occlusive ingredient, such as, for example, coconut oil or petrolatum, before complexing with cyclodextrin. And the fragrance material and the cyclodextrin-fragrance complex may both be coated in some instances.

A scent-releasing system may be employed in the personal care products, wherein the system comprises cyclodextrin complexing material, as described above, in combination with other complexing or encapsulating materials known to the skilled artisan. For example, a scent-releasing system may be employed comprising a combination of cyclodextrin complexing material and one or more additional encapsulating materials. Exemplary encapsulating materials include starches, oligosaccharides, polyethylenes, polyamides, polystyrenes, polyisoprenes, polycarbonates, polyesters, polyacrylates, vinyl polymers, silicas, and aluminosilicates. Commercially available encapsulating materials N-Lok™, manufactured by National Starch, Narlex™ (ST and ST2), and Capsul E™ are useful for the present invention. These materials comprise pregelatinized waxy maize starch and optionally, glucose. The starch is modified by adding monofunctional substituted groups such as octenyl succinic acid anhydride. Accordingly, compositions of the present invention may include a neat fragrance material, a cyclodextrin-fragrance complex, and fragrance material encapsulated with materials other than cyclodextrin, such as those described above. The fragrances of this three-component scent-releasing system may be the same or different. Combining different scent-releasing technologies permits customization of scent expression profiles.

It should be understood that personal care products of the present invention may optionally employ "unloaded" cyclodextrin particles to act as a scavenger for malodor. These optional cyclodextrin particles may or may not have similar properties (or be manufactured using the same techniques) as the complexes described above.

Fragrance Material

Personal care products of the present invention may employ at least one fragrance material that is complexed with the cyclodextrin complexing material discussed above. A representative, non-limiting, list of fragrance materials that may be complexed with the cyclodextrin includes anethole, benzaldehyde, decyl aldehyde, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, methyl benzyl carbinyl acetate, dimethyl benzyl carbinyl acetate, dimethyl phenyl carbinol, eucalyptol, helional, geranial, geraniol, geranyl acetate, geranyl nitrile, cis-3-hexenyl acetate, dihydrocitronellal, d-limonene, linalool, linalool oxide, tetra-hydro linalool, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, phenyl acetaldehyde, alpha-pinene, beta-pinene, gamma-terpinene, terpineol, alpha-terpineol, beta-terpineol, terpinyl acetate, vertenex (para-tertiary-butyl cyclohexyl acetate), gamma-methyl ionone, undecalactone, undecylenic aldehyde, alpha-damascone, beta-damascone, amyl acetate, lemon oil, orange oil, and mixtures thereof.

It may be desirable to include only a single fragrance material (may include a combination of perfumes or other aromatic materials) in the personal care products, and for that fragrance material to be complexed with cyclodextrin.

For these embodiments, the intent is for the consumer to initially perceive (or only minimally perceive) the fragrance material. Such personal care products may be marketed with the following terms: unscented, scent-free, sensitive, and/or hypoallergenic. During use, perspiration or other bodily fluid would release the fragrance material enabling it to be perceived by the consumer.

On the other hand, it may be desirable to include two or more fragrance materials in the personal care product, with at least one the fragrance materials being complexed with the cyclodextrin complexing material and at least one other fragrance material being added as a neat fragrance into the personal care product. In these embodiments, it is preferred for the complexed and neat fragrances to be different from one another. The differences can include types (including, for example, chemical make-up) and numbers of perfumes or other aromatic materials employed in the individual fragrance materials, the concentration level, or both.

The neat or non-complexed fragrance material may include the materials delineated above, or may include other perfumes/aromatic materials known to a person of ordinary skill in the art of creating fragrances. Typical fragrances are described in Arctander, Perfume and Flavour Chemicals (Aroma Chemicals), Vol. I and II (1969) and Arctander, Perfume and Flavour Materials of Natural Origin (1960). U.S. Pat. No. 4,322,308, issued to Hooper et al., Mar. 30, 1982 and U.S. Pat. No. 4,304,679, issued to Hooper et al., Dec. 8, 1981 disclose suitable fragrance materials including, but not limited to, volatile phenolic substances (such as iso-amyl salicylate, benzyl salicylate, and thyme oil red), essence oils (such as geranium oil, patchouli oil, and petitgrain oil), citrus oils, extracts and resins (such as benzoin siam resinoid and opoponax resinoid), "synthetic" oils (such as Bergamot™ 37 and Bergamot™ 430, Geranium™ 76 and Pomeransol™ 314); aldehydes and ketones (such as B-methyl naphthyl ketone, p-t-butyl-A-methyl hydrocinnamic aldehyde and p-t-amyl cyclohexanone), polycyclic compounds (such as coumarin and beta-naphthyl methyl ether), esters (such as diethyl phthalate, phenylethyl phenylacetate, non-anolide 1:4).

EXAMPLES

The following examples further describe and demonstrate embodiments within the scope of the present invention. The examples are given solely for the purpose of illustration and are not to be construed as limitations of the present invention as many variations thereof are possible without departing from the spirit and scope of the invention.

Example 1: Deodorant Stick

| Ingredient | Example 1, wt % |
| --- | --- |
| Dipropylene Glycol | Quantity Sufficient |
| Propylene Glycol | 17.80 |
| Water | 21.70 |
| Sodium Stearate | 5.50 |
| Petrolatum Coated Spray Dried Cyclodextrin Fragrance Complex | 1.25 |
| Tetra Sodium EDTA | 0.50 |
| PPG-3 Myristyl Ether | 0.04 |
| Neat Perfume | 3.00 |

Example 1 can be made as follows: Petrolatum coated cyclodextrin fragrance complexes are prepared by combining spray dried complex particles with petrolatum (e.g., super white protopet manufactured by Witco) at a ratio of 1:1 in a Hamilton Beach custom grind coffee grinder (model 80365). Turn the grinder to the highest speed and mix until the petrolatum fully coats the spray dried cyclodextrin fragrance complex particles. The mixture may have a paste-like consistency. In a suitable vessel, combine all solvents (propylene glycol, dipropylene glycol, water), gellants (sodium stearate, Witconol APM) and tetrasodium EDTA and then heat to 80° C. while mixing. Then add the petrolatum coated complex paste and mix. Cool the mixture to 70° C., and then add the neat perfume. Cool the mixture to 65° C. and pour into deodorant canisters.

Examples 2 and 3: Personal Cleansing Bar

| Ingredient | Example 2, wt % | Example 3, wt % |
| --- | --- | --- |
| Soap | 80.15 | 63.26 |
| Free Fatty Acid | 5.00 | 4.29 |
| Water | 10.69 | 7.50 |
| Sodium Chloride | 1.11 | 0.90 |
| Titanium Dioxide | 0.25 | 0.25 |
| Spray Dried Cyclodextrin Fragrance Complex | 2.00 | 2.00 |
| Neat Perfume | 0.80 | 0.80 |
| Potassium Alkyl Sulfate | | 10.00 |
| Sodium Laureth 3 Sulfate | | 3.00 |
| Magnesium Silicate | | 7.50 |
| Misc. | | 0.50 |

Examples 2 and 3 can be made as follows: mix the complexed fragrance and the neat perfume into dried soap noodles in an amalgamator. Process the material, for example, by milling through a 3-roll soap mill, to obtain a homogenous mixture of perfume and soap flakes. The material is then processed on a plodder and stamped into a soap bar.

Example 4: Aerosol Antiperspirant

| Ingredient | Example 4, wt % |
| --- | --- |
| Aluminum Chlorohydrate | 12.00 |
| Cyclopentasiloxane | 17.45 |
| Dimethicone | 2.01 |
| Spray Dried Cyclodextrin Fragrance Complex | 3.00 |
| Isopropyl Myristate | 4.00 |
| Quaternium-18 Hectorite | 1.00 |
| Propylene Carbonate | 0.33 |
| n-Butane A-17 | Quantity Sufficient |
| Hydrofluorocarbon | 20.29 |
| Neat Perfume | 0.50 |

The present invention includes antiperspirant and/or deodorant compositions, as shown by Example 1 above. A broader discussion of antiperspirant/deodorant compositions, in accordance with the present invention, is now provided. These compositions typically comprise a liquid carrier material. Suitable liquid carriers include, but are not limited to, any topically safe and effective organic, silicone-containing or fluorine-containing, volatile or non-volatile, polar or non-polar liquid carrier. The liquid carrier is preferably liquid under ambient conditions, and can include one or more liquid carrier materials provided that the any such combination of materials is in liquid form under ambient conditions. Depending on the type of product form desired, concentrations of the liquid carrier in the compositions will typically range from about 10% or from about 30% to about 90% or to about 75%, by weight of the composition. The antiperspirant/deodorant compositions may be formulated as an aqueous or anhydrous composition. Aqueous compositions may comprise from about 10% or from about 15% water, by weight of the composition to about 75%, to about 60%, or to about 50% water, by weight of the composition. Anhydrous compositions may comprise less than about 10%, less than about 3%, less than about 1%, or zero percent water, by weight of the composition.

The antiperspirant/deodorant compositions typically also include an active. By way of example only, the antiperspirant actives may include astringent metallic salts, especially inorganic and organic salts of aluminum, zirconium and zinc, as well as mixtures thereof. A representative, non-limiting list of suitable deodorant actives includes ethylenediaminetetraacetic acid, cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4,4'-trichlorocarbanilide (triclocarban), L-lysine hexadecyl amide, zinc pyrithione, zinc phenolsulfate, farnesol, and mixtures thereof.

Exemplary antiperspirant/deodorant compositions also comprise thickening agents to help provide the composition with the desired viscosity, rheology, texture and/or product hardness, or to otherwise help suspend any dispersed solids or liquids within the composition. The term "thickening agent" may include any material known or otherwise effective in providing suspending, gelling, viscosifying, solidifying or thickening properties to the composition or which otherwise provide structure to the final product form. These thickening agents may include gelling agents, polymeric or nonpolymeric agents, inorganic thickening agents, or viscosifying agents. The thickening agents may include organic solids, silicone solids, crystalline or other gellants, inorganic particulates such as clays or silicas, or combinations thereof. The concentration and type of the thickening agent selected for use in the antiperspirant/deodorant composition will vary depending upon the desired product form, viscosity, and hardness. The thickening agents suitable for use herein, may have a concentration range from at least about 0.1%, at least about 3%, or at least about 5% but no more than about 35%, no more than about 20%, or no more than about 10%, by weight of the composition. Non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof.

The antiperspirant/deodorant compositions may further comprise one or more optional components which may modify the physical or chemical characteristics of the compositions or serve as additional "active" components when deposited on the skin. Of course, such optional components may be included provided that they are physically and chemically compatible and do not otherwise unduly impair product stability, aesthetics, or performance. Nonlimiting examples of such optional materials include, but are not limited to, pH buffering agents, malodor controlling agents, fragrance materials, emollients, humectants, soothing agents, dyes and pigments, medicaments, baking soda and related materials, preservatives, and soothing agents such as aloe vera, allantoin, D-panthenol, pantothenic acid derivatives (e.g., those disclosed in U.S. Pat. No. 6,495,149), avocado oil and other vegetative oils, and lichen extract.

The antiperspirant/deodorant compositions may be made in a variety of forms including, for example, solid, soft solid, spray, roll-on, and aerosol. Aerosol products employ a propellant in the composition. Exemplary propellants include dimethyl ether, carbon dioxide, nitrous oxide, 1,1 difluoroethane, 1,1,1,2 tetrafluoro ethane, butane, isobutane, pentane, isopentane, propane, and mixtures thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care product, comprising:
   (a) a liquid carrier;
   (b) a plurality of particles dispersed within the liquid carrier, the plurality of particles comprising a cyclodextrin complexing material and a first fragrance material, wherein the percent of the first fragrance material that is complexed with the cyclodextrin is greater than about 75%, so that the perceptibility of the first fragrance is minimized prior to its release; and
   (c) a second fragrance material that is not complexed with the cyclodextrin and that is different from the first fragrance material,
      wherein the composition or article does not contain an antiperspirant active;
      and wherein the plurality of particles are formed using a process comprising a step of spray drying.

2. The personal care product of claim 1, wherein the percent of the first fragrance material that is complexed with the cyclodextrin is greater than about 95%.

3. The personal care product of claim 1, wherein the personal care product is a deodorant.

4. The personal care product of claim 3, wherein the deodorant is in the form selected from the group consisting of a solid, soft solid, spray, roll-on, and aerosol.

5. The personal care product of claim 1, wherein at least some of the plurality of particles comprise a coating material.

6. The personal care product of claim 5, wherein the coating material is selected from the group consisting of hydrocarbons, waxes, petrolatum, silicones, partially or fully esterfied sucrose esters, polyglycerol esters, and mixtures thereof.

7. The personal care product of claim 1, further comprising additional cyclodextrin particles that do not contain a fragrance material.

8. The personal care product of claim 1, further comprising a third fragrance material that is encapsulated with a material other than cyclodextrin.

9. The personal care product of claim 8, wherein the material other than cyclodextrin is selected from the group consisting of starches, oligosaccharides, polyethylenes, polyamides, polystyrenes, polyisoprenes, polycarbonates, polyesters, polyacrylates, vinyl polymers, silicas, aluminosilicates, and mixtures thereof.

10. The personal care product of claim 1, wherein the percent of the first fragrance material that is complexed with the cyclodextrin is 96% or greater.

11. The personal care product of claim 1, further comprising a plurality of particles comprising a cyclodextrin complexing material and a third fragrance material, wherein the percent of the third fragrance material that is complexed with the cyclodextrin is greater than about 90% and wherein the third fragrance material is different from the first fragrance material.

* * * * *